(12) United States Patent
Chien

(10) Patent No.: US 10,350,117 B2
(45) Date of Patent: Jul. 16, 2019

(54) SANITARY NAPKIN WITH FOLDABLE FLOW-GUIDE UNIT

(71) Applicant: Yuan-Cheng Chien, Kaohsiung (TW)

(72) Inventor: Yuan-Cheng Chien, Kaohsiung (TW)

( * ) Notice: Subject to any disclaimer, the term of this patent is extended or adjusted under 35 U.S.C. 154(b) by 375 days.

(21) Appl. No.: 15/263,426

(22) Filed: Sep. 13, 2016

(65) Prior Publication Data

US 2017/0367904 A1    Dec. 28, 2017

(30) Foreign Application Priority Data

Jun. 24, 2016  (TW) .............................. 105119868 A

(51) Int. Cl.
  *A61F 13/47*    (2006.01)
  *A61F 13/472*   (2006.01)
  *A61F 13/511*   (2006.01)

(52) U.S. Cl.
  CPC .... *A61F 13/47272* (2013.01); *A61F 13/4704* (2013.01); *A61F 13/47218* (2013.01); *A61F 13/51104* (2013.01); *A61F 13/51108* (2013.01)

(58) Field of Classification Search
  CPC ............ A61F 13/4704; A61F 13/47218; A61F 13/47272; A61F 13/4752; A61F 13/4755; A61F 13/49446; A61F 13/4946; A61F 13/49493; A61F 13/51104; A61F 13/51108
  See application file for complete search history.

(56) References Cited

U.S. PATENT DOCUMENTS

| | | | | |
|---|---|---|---|---|
| 3,101,714 A | * | 8/1963 | Penska | A61F 13/2051 604/377 |
| 5,575,785 A | * | 11/1996 | Gryskiewicz | A61F 13/49426 604/385.28 |
| 2005/0267433 A1 | * | 12/2005 | Tanio | A61F 13/47272 604/385.17 |
| 2007/0118090 A1 | * | 5/2007 | Kawamura | A61F 13/47218 604/385.101 |
| 2008/0172018 A1 | * | 7/2008 | Chien | A61F 13/47227 604/385.04 |
| 2014/0025028 A1 | * | 1/2014 | Stewart | A61F 13/47218 604/385.03 |
| 2015/0173969 A1 | * | 6/2015 | Goldsmith | A61F 13/475 604/360 |

FOREIGN PATENT DOCUMENTS

| | | |
|---|---|---|
| CN | 101234056 A | 8/2008 |
| CN | 101234058 A | 8/2008 |

* cited by examiner

*Primary Examiner* — Kathryn E Ditmer
(74) *Attorney, Agent, or Firm* — Alan D. Kamrath; Mayer & Williams PC

(57) ABSTRACT

A sanitary napkin includes a main pad body having an absorbent body, and a flow-guide unit including two flow-guide members having bottom ends connected to a top surface of the absorbent body, and a pull piece connected to top ends of the flow-guide members. Each flow-guide member includes a plurality of flow-guide sections foldably connected to each other, and a plurality of outer junction sections each formed between outer ends of two adjacent ones of the flow-guide sections. The pull piece is pulled to move the flow-guide sections relative to the absorbent body from a folded position, in which the flow-guide sections are stacked one upon the other, to an extended position, in which the outer junction sections of the flow-guide members are configured to contact the buttocks of a user.

13 Claims, 18 Drawing Sheets

SANITARY NAPKIN WITH FOLDABLE FLOW-GUIDE UNIT

CROSS-REFERENCE TO RELATED APPLICATION

Pursuant to 35 U.S.C. § 119(a), this application claims the benefit of the priority to Taiwan Patent Application No. 105119868 filed Jun. 24, 2016. The content of the prior application is incorporated herein by its entirety.

BACKGROUND OF THE INVENTION

1. Field of the Invention

The invention relates to a hygiene product and, more particularly, to a sanitary napkin used by women.

2. Description of the Prior Arts

Sanitary napkins help women to have a better quality of life during menstruation. After many years of research and development, the design of the sanitary napkin is diversified to enhance different levels of comfort. The sanitary napkin for nighttime use has a length extending to a rear section of the intergluteal cleft of the user. As such, leakage of the menstrual blood from the rear section of the intergluteal cleft of the user can be prevented during sleep. However, the blood is not immediately absorbed by the sanitary napkin when the posture of the user is inclined during sleep, so that there is still apprehension that the menstrual blood may leak.

Referring to FIGS. 1 and 2, a sanitary napkin 1, as disclosed in People's Republic of China Patent Publication No. 101234056, includes a main body 11 and a folded flow-guide strip 12 disposed on the main body 11. To use the sanitary napkin 1, the flow-guide strip 12 is pulled upward, and is then placed at the intergluteal cleft of the user. When the menstrual blood flows into the intergluteal cleft, the menstrual blood is absorbed by the flow-guide strip 12. Comfort can be enhanced and the risk of blood leakage can be reduced during use of the sanitary napkin 1. However, the flow-guide strip 12 is connected to an outer cover piece 14 which covers an absorbent body 13, so that the menstrual blood absorbed by the flow-guide strip 12 must pass through the outer cover piece 14 before being absorbed by the absorbent body 13. In view of this, the absorption rate of the sanitary napkin 1 appears to be slow.

Referring to FIGS. 3 and 4, a sanitary napkin 2, as disclosed in People's Republic of China Patent Publication No. 101234058, includes an absorbent body 21, an outer cover piece 22 covering the absorbent body 21, a liquid-blocking piece 24 disposed at the center of the outer cover piece 22 and defining a groove 23, a flow-guide strip 25 connected to the liquid-blocking piece 24, and a pull string 26 inserted into the flow-guide strip 25. A user can pull the pull string 26 to pull the folded flow-guide strip 25 upward, so that the effect of quickly absorbing the menstrual blood can be achieved. However, the flow-guide strip 25 is connected to the liquid-blocking piece 24, so that the menstrual blood absorbed by the flow-guide strip 25 must first pass through the liquid-blocking piece 24 and the outer cover piece 22 before being absorbed by the absorbent body 21. In view of this, the absorption rate of the sanitary napkin 2 also appears to be slow.

SUMMARY OF THE INVENTION

Therefore, an objective of the present invention is to provide a sanitary napkin that is capable of overcoming the aforesaid drawback of the prior arts.

Accordingly, a sanitary napkin of this invention includes a main pad body and a flow-guide unit disposed on the main pad body. The main pad body includes a lower pad layer, an absorbent body disposed on the lower pad layer, and an upper pad layer cooperating with the lower pad layer to confine the absorbent body therebetween.

The flow-guide unit includes two flow-guide members and a pull piece. Each flow-guide member has a top end and a bottom end. The bottom ends of the flow-guide members are connected to a top surface of the absorbent body and are spaced apart from each other. Each flow-guide member includes a plurality of flow-guide sections, with the flow-guide sections stacked in a top-bottom direction and foldably connected to each other, a plurality of inner junction sections each formed between inner ends of two adjacent ones of the flow-guide sections, and a plurality of outer junction sections each formed between outer ends of two adjacent ones of the flow-guide sections. The pull piece is connected to the top ends of the flow-guide members, and is pulled to move the flow-guide sections relative to the absorbent body from a folded position, in which the flow-guide sections of each flow-guide member are stacked one upon the other, to an extended position, in which the outer junction sections of each flow-guide member are spaced apart from each other and in which the outer junction sections of the flow-guide members are configured to contact the buttocks of a user.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
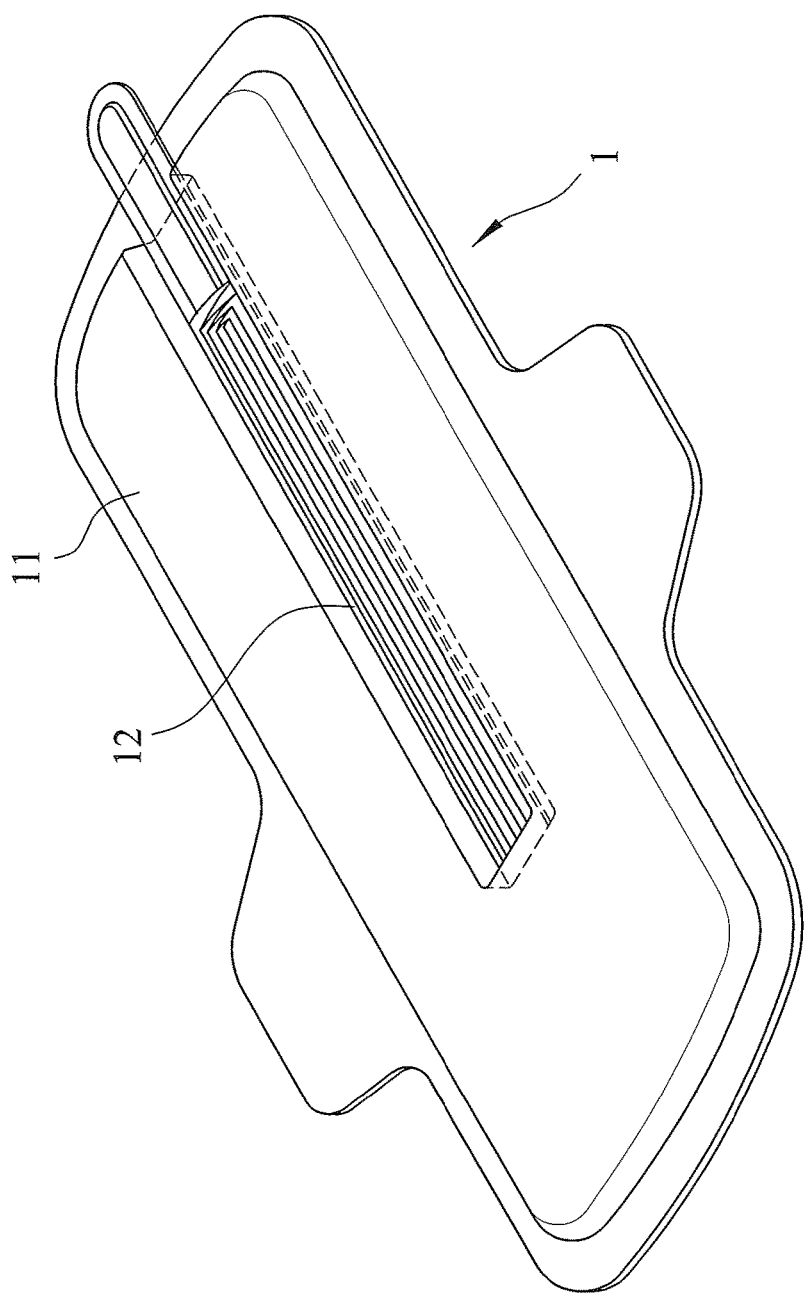
FIG. 1 is a perspective view of a sanitary napkin disclosed in People's Republic of China Patent Publication No. 101234056.
Figure 2:
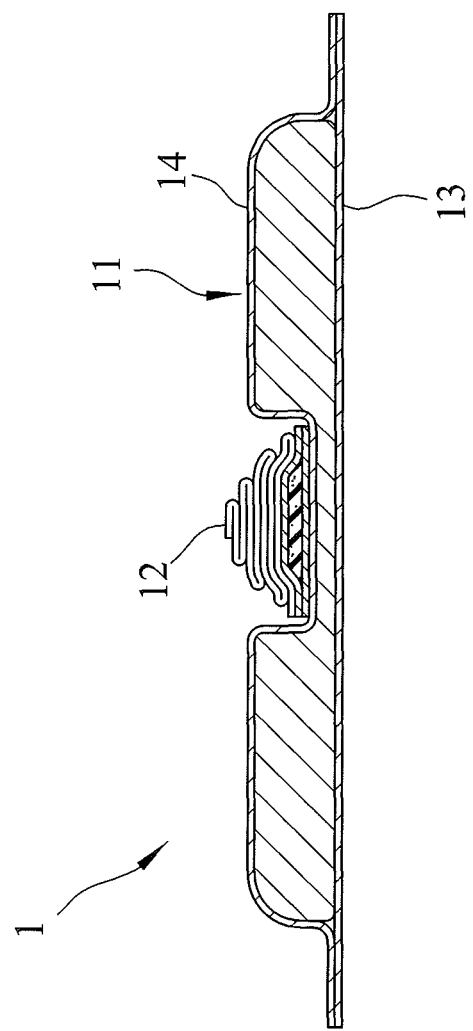
FIG. 2 is a sectional view of FIG. 1.
Figure 3:
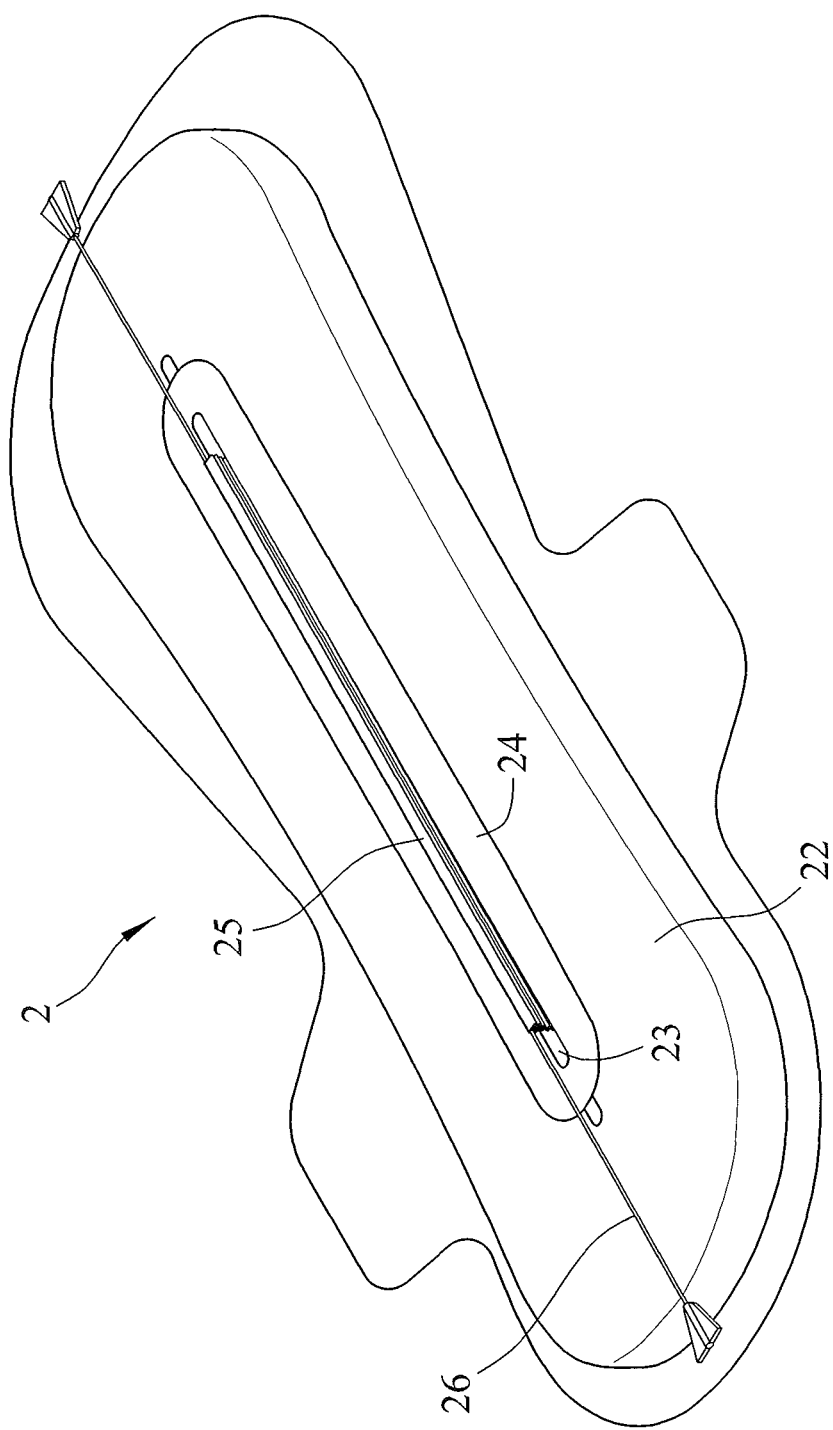
FIG. 3 is a perspective view of a sanitary napkin disclosed in People's Republic of China Patent Publication No. 101234058.
Figure 4:
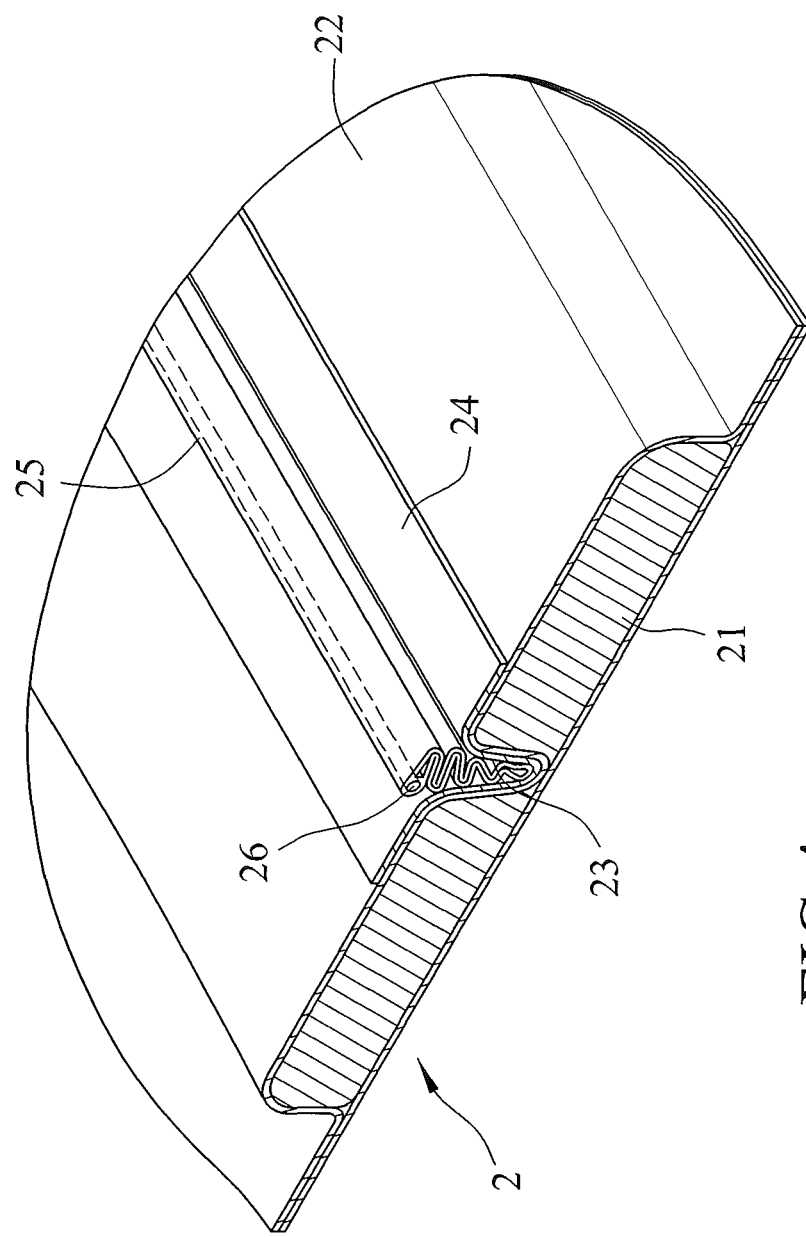
FIG. 4 is a fragmentary sectional view of a portion of FIG. 3.

Before the present invention is described in greater detail with reference to the accompanying embodiments, it should be noted herein that like elements are denoted by the same reference numerals throughout the disclosure.

Referring to FIGS. 5 to 11, a sanitary napkin 3 according to the first embodiment of the present invention is shown to include a main pad body 4 and a flow-guide unit 5 disposed on the main pad body 4.

Figure 9:
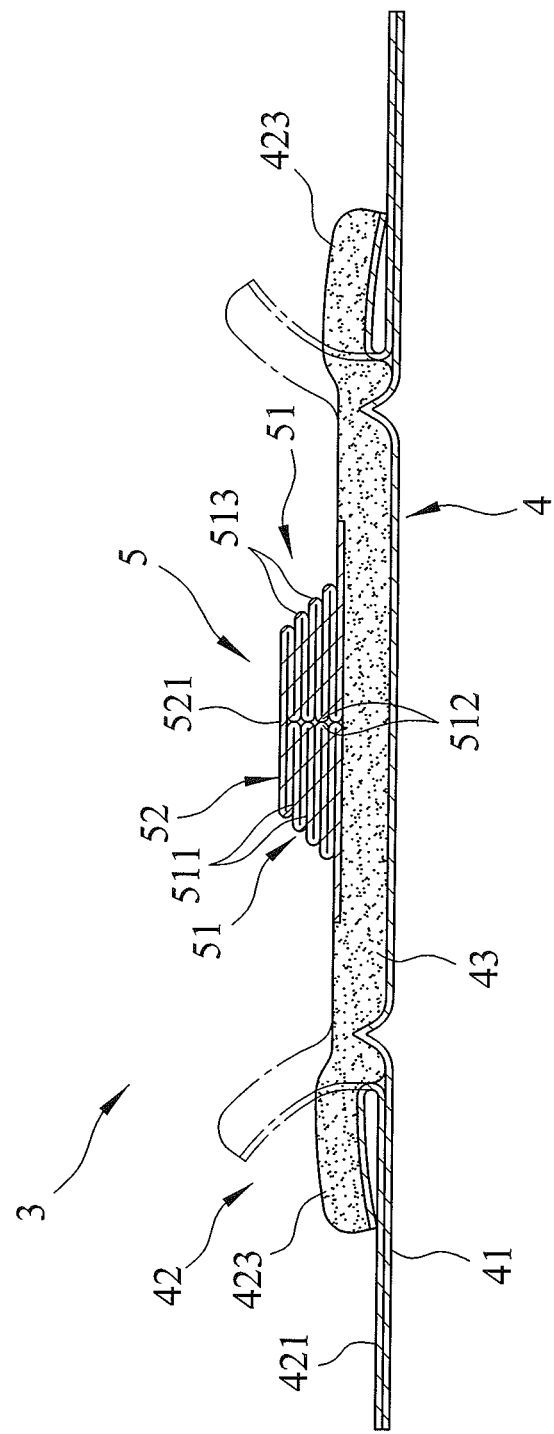
FIG. 9 is a schematic view similar to FIG. 8, but with two liquid-blocking portions turned inside out relative to a connecting portion.

The main pad body 4 includes a lower pad layer 41, an absorbent body 43 disposed on the lower pad layer 41, and an upper pad layer 42 cooperating with the lower pad layer 41 to confine therebetween the absorbent body 43. The upper pad layer 42 has an annular connecting portion 421 connected to the lower pad layer 41, and two liquid-blocking portions 423 that extend inwardly from an inner periphery of the connecting portion 421, that are disposed on a top surface of the absorbent body 43, and that are spaced apart from each other in a left-right direction. The connecting portion 421 surrounds the liquid-blocking portions 423. Each of the liquid-blocking portions 423 is turnable inside out relative to the connecting portion 421, as shown in solid lines in FIG. 9, to expose the entire top surface of the absorbent body 43. The connecting portion 421 and an outer side of each liquid-blocking portion 423 are similarly made of a liquid impermeable material, while the absorbent body 43 and an inner side of each liquid-blocking portion 423 are similarly made of a liquid-absorbing material. As such, when the liquid-blocking portions 423 are turned inside out, as shown in FIG. 9, the entire top surface of the absorbent body 43 is not only exposed, but an absorbing area of the main pad body 4 can be extended from the top surface of the absorbent body 43 to the inner sides of the liquid-blocking portions 423 as well. Hence, the absorption capacity of the sanitary napkin 3 can be effectively enlarged, and the sanitary napkin 3 is suitable for use by different kinds of users.

Figure 5:
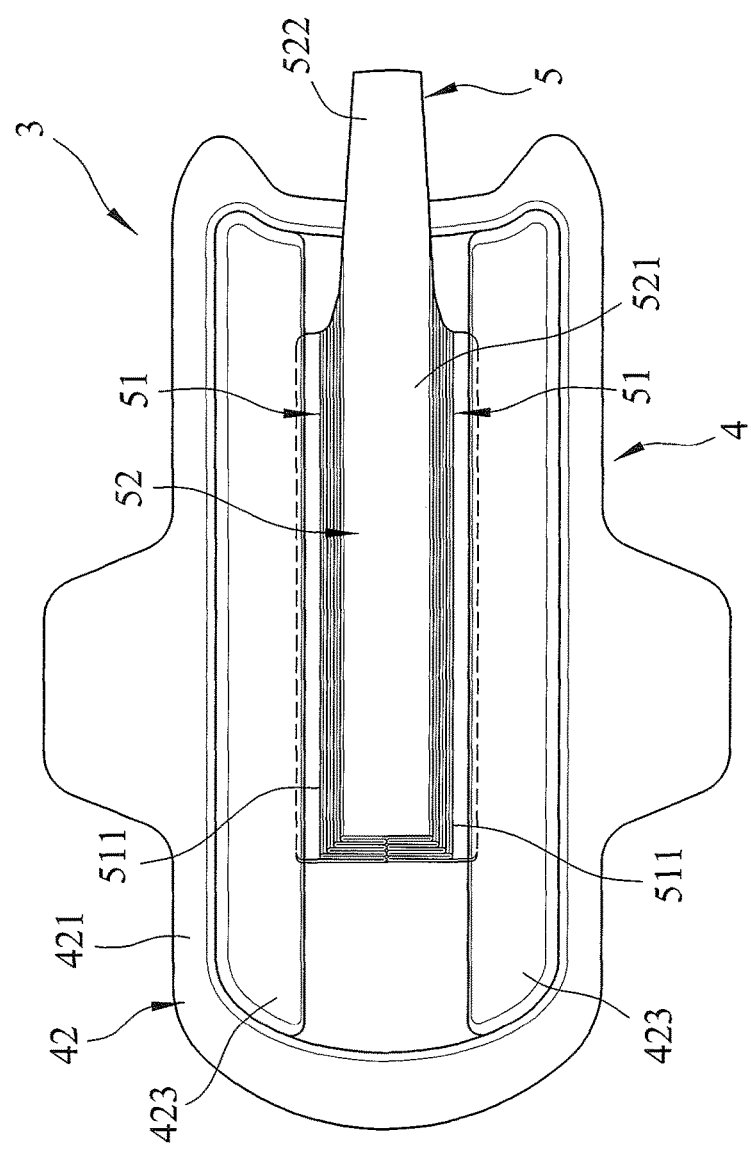
FIG. 5 is a top view of a sanitary napkin according to the first embodiment of the present invention.
Figure 8:
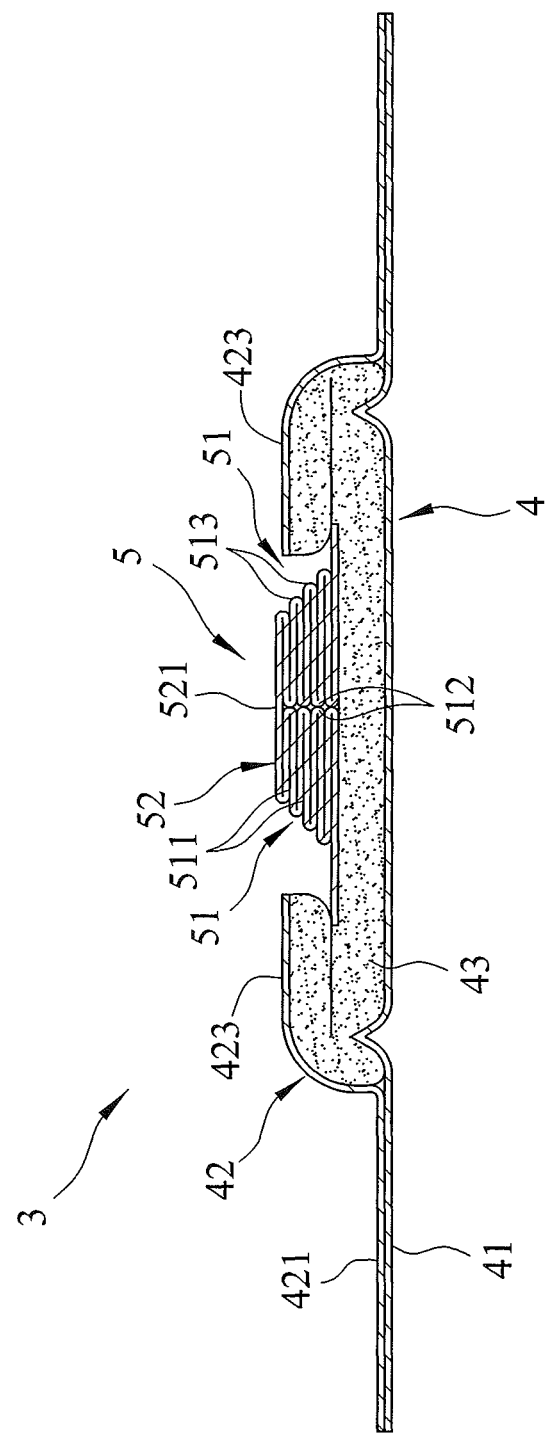
FIG. 8 is a sectional view of the first embodiment, illustrating flow-guide sections of flow-guide members in a folded position.
Figure 10:
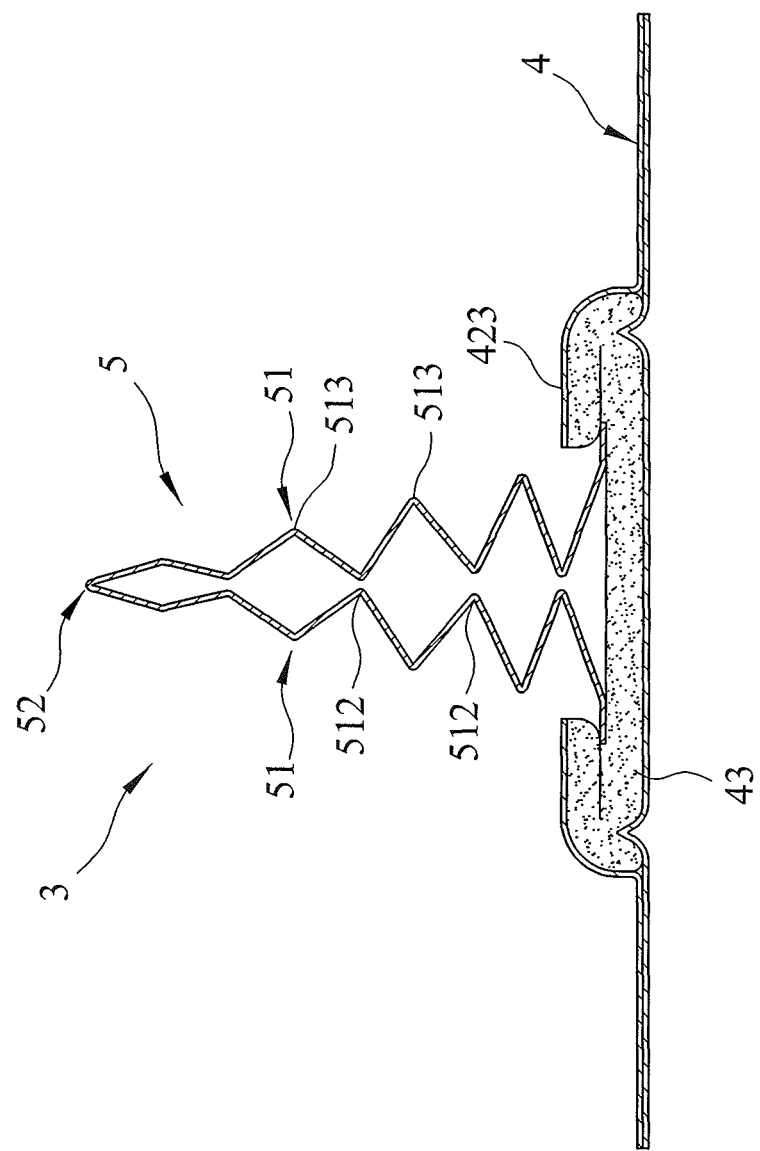
FIG. 10 is a view similar to FIG. 8, but with a pull piece pulled upward to move the flow-guide sections of the flow-guide members from the folded position to an extended position.

The flow-guide unit 5 includes two flow-guide members 51 and a pull piece 52. Each of the flow-guide members 51 has a top end and a bottom end. The bottom ends of the flow-guide members 51 are directly connected to the top surface of the absorbent body 43 and are spaced apart from each other, as shown in FIGS. 8 and 10. The liquid-blocking portions 423 are respectively proximate to the bottom ends of the flow-guide members 51. Each flow-guide member 51 includes a plurality of flow-guide sections 511, a plurality of inner junction sections 512 each formed between inner ends of two adjacent ones of the flow-guide sections 511, and a plurality of outer junction sections 513 each formed between outer ends of two adjacent ones of the flow-guide sections 511. The flow-guide sections 511 of each flow-guide member 51 abut against each other, are stacked in a top-bottom direction, and are connected foldably to each other. Each flow-guide section 511 has a length extending in a front-rear direction, and a width extending in the left-right direction. The pull piece 52 has a main body portion 521 connected to the top ends of the flow-guide members 51, and a rear extension portion 522 extending integrally and rearwardly from a rear end of the main body portion 521 and out of the main pad body 4, as shown in FIGS. 5 and 6.

Figure 6:
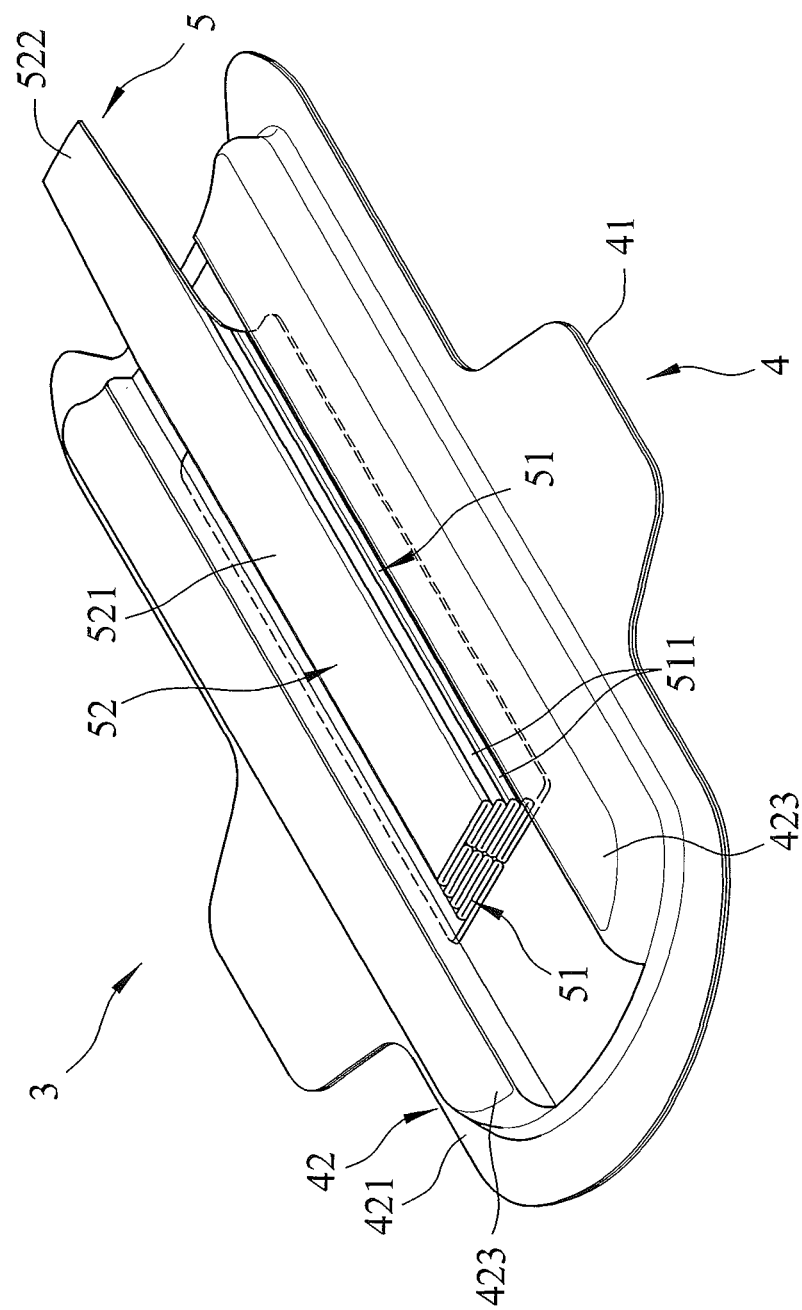
FIG. 6 is a perspective view of the first embodiment.
Figure 7:
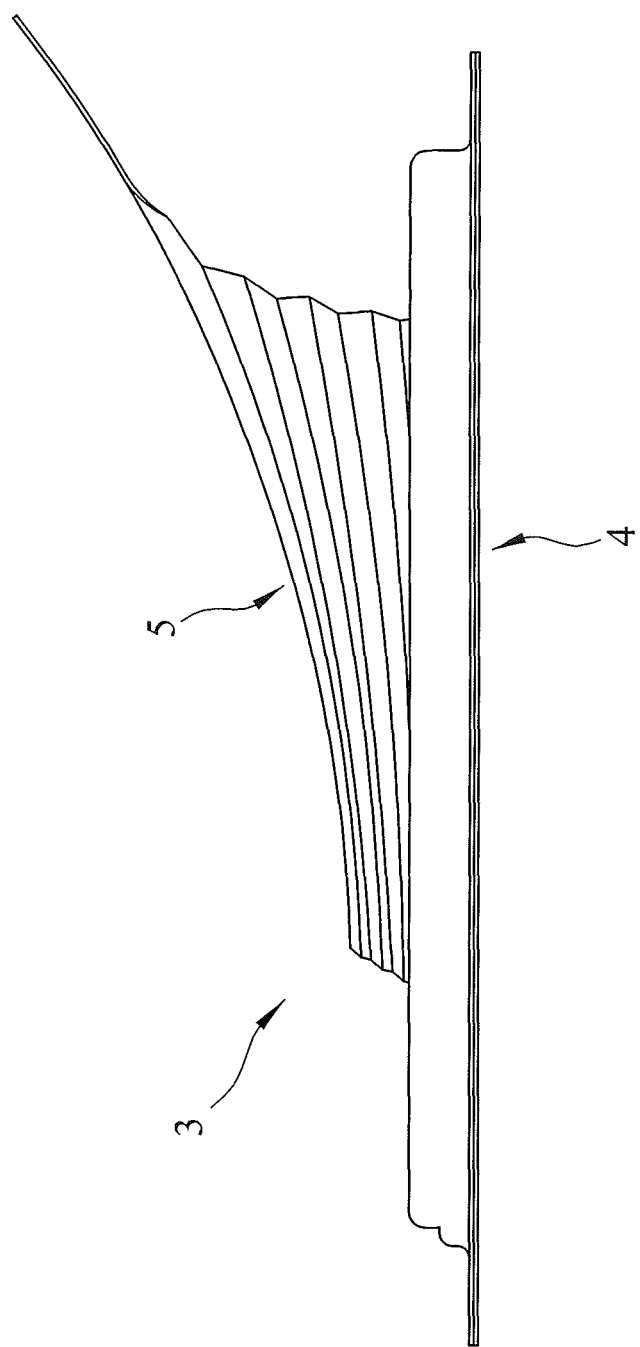
FIG. 7 is a view of the lateral aspect of the first embodiment.

With reference to FIGS. 6, 8 and 10, the rear extension portion 522 of the pull piece 52 is pulled by the user to move upward the flow-guide sections 511 of the flow-guide members 51 relative to the absorbent body 43 from a folded position, as shown in FIGS. 6 and 8, to an extended position, as shown in FIG. 10. In the folded position, the flow-guide sections 511 of each flow-guide member 51 abut against each other and are stacked in the top-bottom direction. The flow-guide sections 511 of the flow-guide members 51 are symmetrically disposed, and the inner junction sections 512 thereof are proximate to each other, so that a space occupied by the flow-guide members 51 can be reduced when the flow-guide sections 511 are in the folded position.

Figure 11:
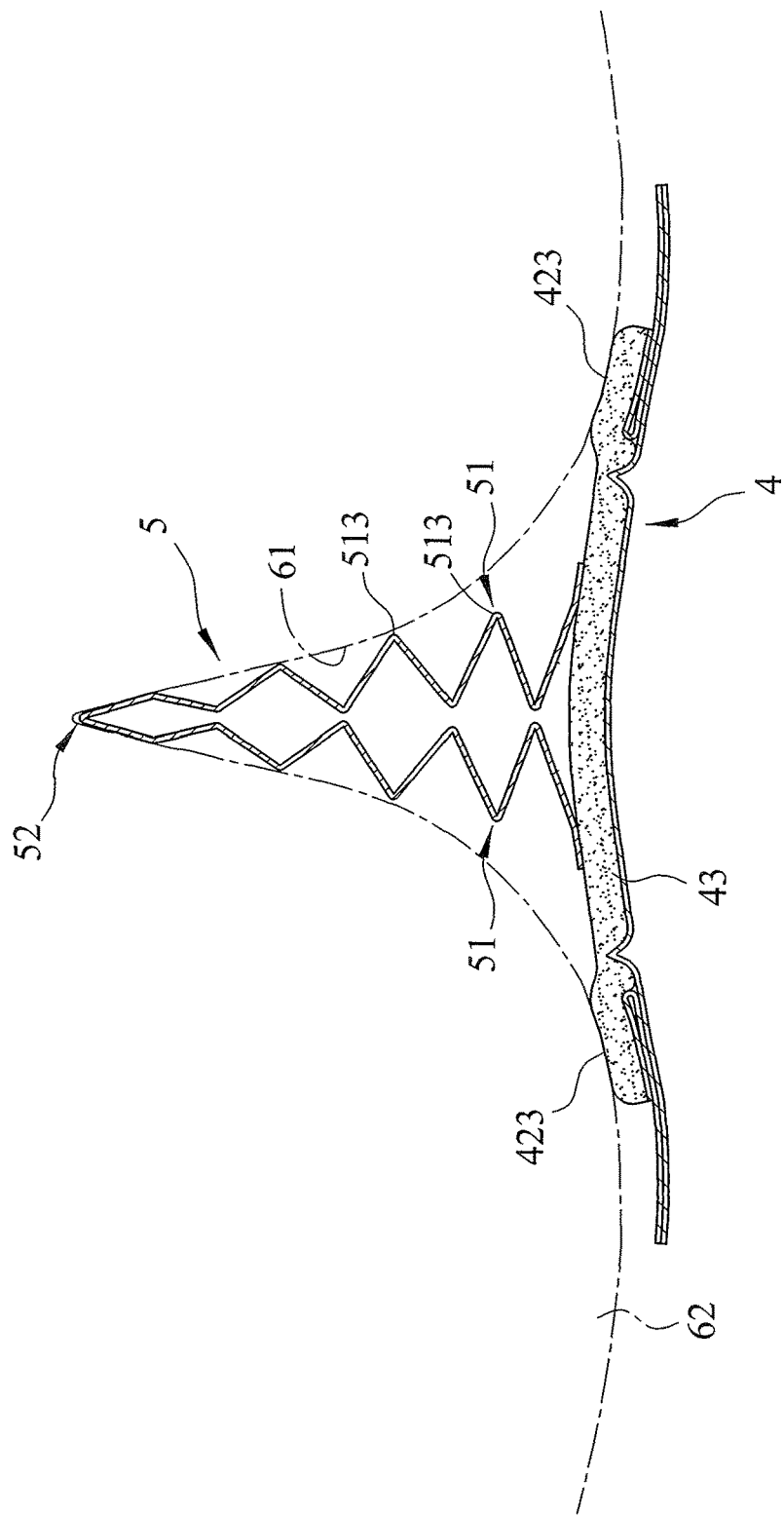
FIG. 11 is a sectional view, illustrating the first embodiment in a state of use.

In the extended position, the flow-guide sections 511 of each flow-guide member 51 are spaced apart from each other, and the angles of the inner junction sections 512 and of the outer junction sections 513 are enlarged, as shown in FIG. 10. It should be noted herein that when the pull piece 52 is pulled to the extreme, the flow-guide sections 511 of the flow-guide members 51 are straightened such that they are parallel to each other. The flow-guide members 51 and the pull piece 52 are integrally formed of the same material. Further, when the rear extension portion 522 of the pull piece 52 is pulled, the pull piece 52 has an inverted V-shaped cross section, as shown in FIG. 10. In use, as shown in FIG. 11, the flow-guide members 51 are located in the intergluteal cleft 61 of the user, and some of the outer junction sections 513 of the flow-guide members 51 are in contact with the user's buttocks 62, so that the menstrual blood flowing along the intergluteal cleft 61 can be easily absorbed by the flow-guide members 51.

Since the flow-guide members 51 are directly connected to the absorbent body 43, the sanitary napkin 3 has a strong absorption ability and can maintain dryness. Further, when the liquid-blocking portions 423 are turned inside out so that the inner sides thereof face the user's buttocks 62, an absorbing area of the sanitary napkin 3 can be increased to thereby enhance the absorbing ability thereof. It should be noted herein that, when the flow-guide sections 511 of the flow-guide members 51 are in the folded position, as shown in FIG. 6, the widths of the flow-guide sections 511 of each flow-guide member 51 gradually decrease from bottom to top, so that when the pull piece 52 is pulled to move the flow-guide sections 511 to the extended position, as shown in FIG. 11, the distances between the outer junction sections 513 of one of the flow-guide members 51 and their corresponding outer junction sections 513 of the other flow-guide member 51 gradually reduce from bottom to top. That is, the outer junction sections 513 of the flow-guide members 51 form a tapered profile, so that the flow-guide members 51 can be easily disposed in and fit the intergluteal cleft 61 of the user.

The rear extension portion 522 of the pull piece 52 can be pulled upward by the user to move the flow-guide members 51 into the intergluteal cleft 61 and close to the private part of the user. The flow-guide unit 5 is provided with the two flow-guide members 51, so that users having big buttocks can also be accommodated. Further, the flow-guide members 51 can quickly absorb the menstrual blood flowing into the intergluteal cleft 61 and guide the blood to the absorbent body 43 during sleep of the user and even when she frequently alters her sleeping postures, so that leakage of the blood can be prevented and dryness can be maintained.

Moreover, the rear extension portion 522 of the pull piece 52 is clamped at a rear side of the intergluteal cleft 61, so that when the user walks, the flow-guide members 51 will not be displaced. Because the flow-guide members 51 are directly disposed in the intergluteal cleft 61 of the user, the upper pad layer 42 does not need to be in close contact with the user's buttocks 62, so that a ventilation effect can be achieved.

Figure 12:
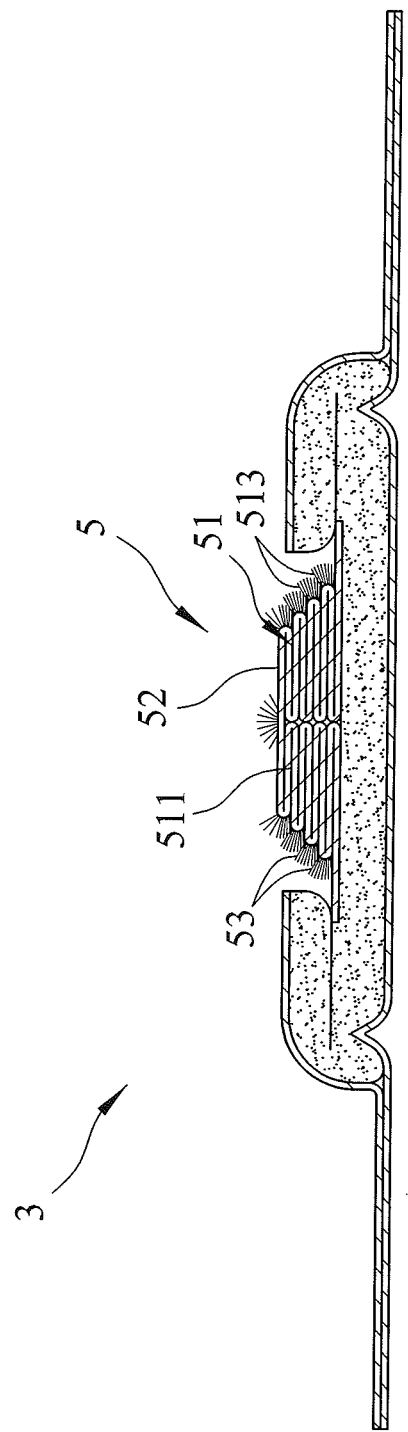
FIG. 12 is a sectional view of the second embodiment of the sanitary napkin of the present invention.
Figure 13:
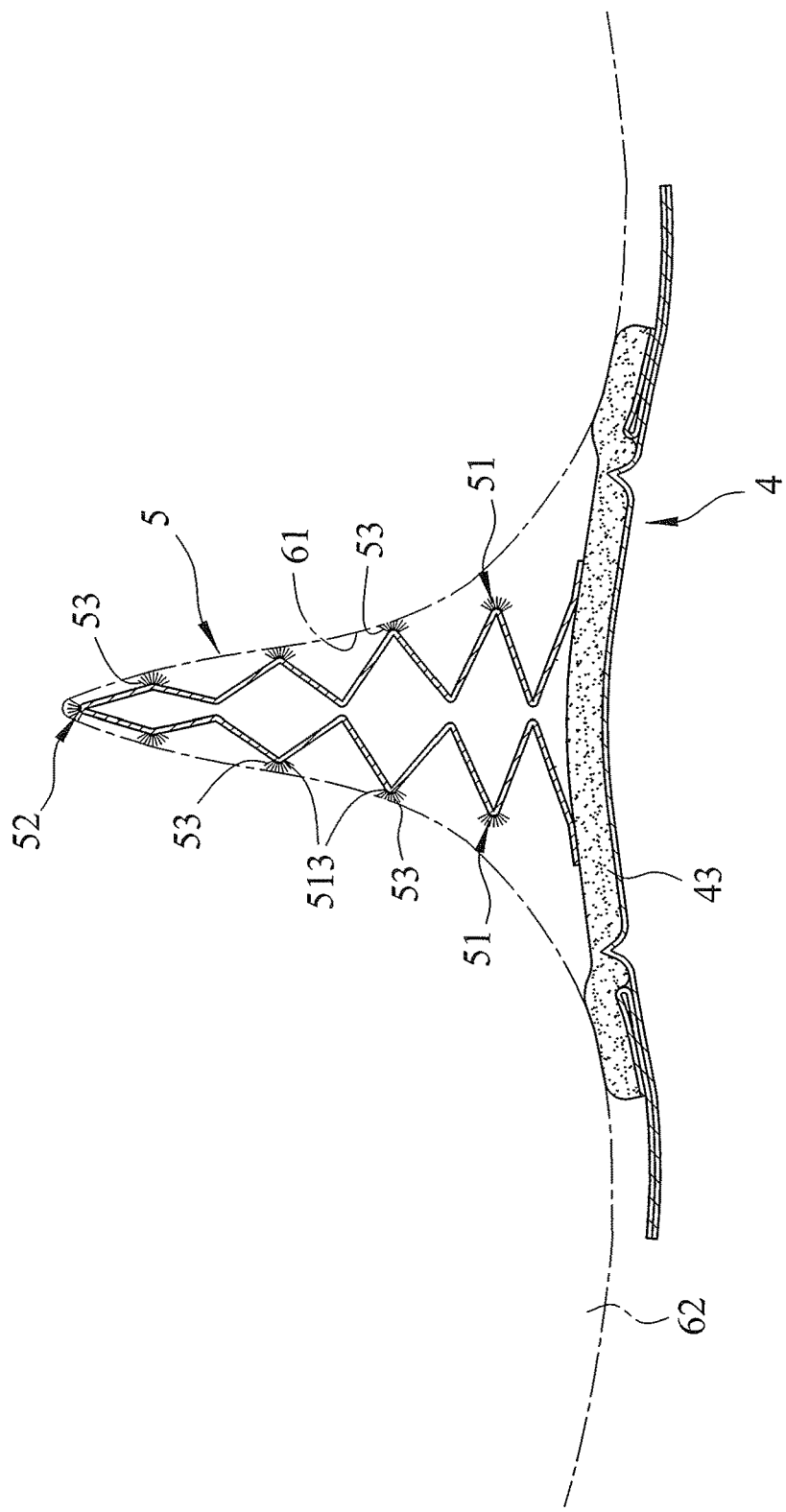
FIG. 13 is a sectional view of the second embodiment in a state of use.

Referring to FIGS. 12 and 13, the second embodiment of the sanitary napkin 3 of this invention is shown to be generally identical to the first embodiment. However, in this embodiment, the flow-guide unit 5 further includes a plurality of liquid-absorbent fluffs 53 provided on the outer junction sections 513 of the flow-guide members 51 and on an intermediate portion of the pull piece 52. When the pull piece 52 is pulled to move the flow-guide members 51 into the intergluteal cleft 61, the liquid-absorbant fluffs 53 can contact the user's buttocks 62, as shown in FIG. 13, thereby enhancing the comfort in use of the sanitary napkin 3 of this invention.

Figure 14:
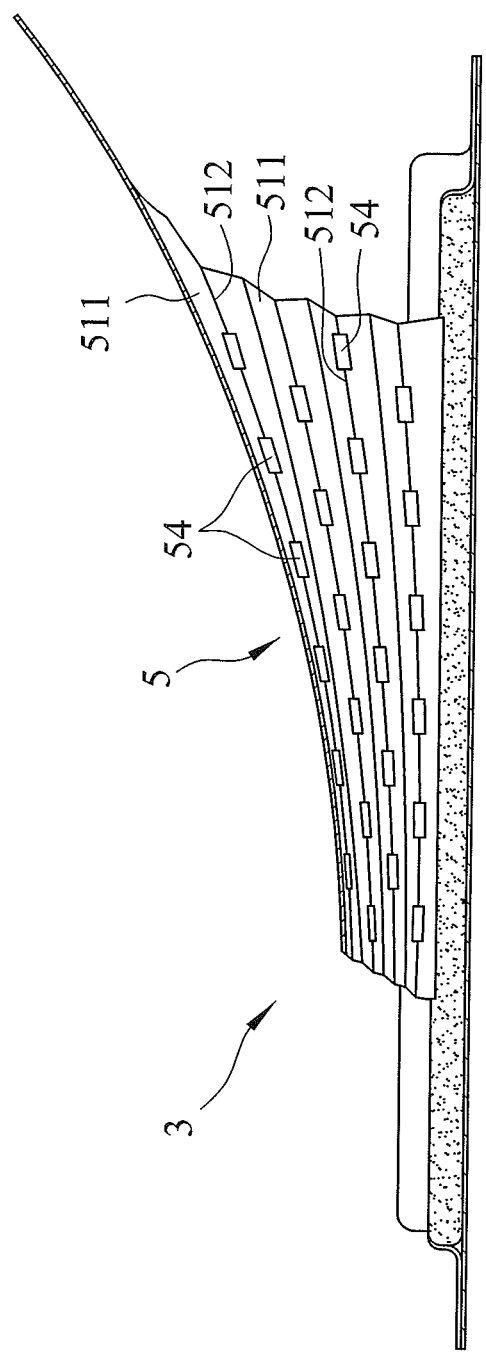
FIG. 14 is a sectional view of the third embodiment of the sanitary napkin of the present invention.

Referring to FIG. 14, the third embodiment of the sanitary napkin 3 of this invention is shown to be generally identical to the first embodiment. However, in this embodiment, each flow-guide member 51 of the flow-guide unit 5 further includes a plurality of vent holes 54 formed in the inner junction sections 512. The vent holes 54 formed in each of the inner junction sections 512 are spaced apart from each other in a front-rear direction. The vent holes 54 in two adjacent ones of the inner junction sections 512 are staggered with respect to each other. The vent holes 54 are provided for ventilation purposes to prevent the user from feeling sultry, thereby enhancing the comfort in use of the sanitary napkin 3 of this invention.

Figure 15:
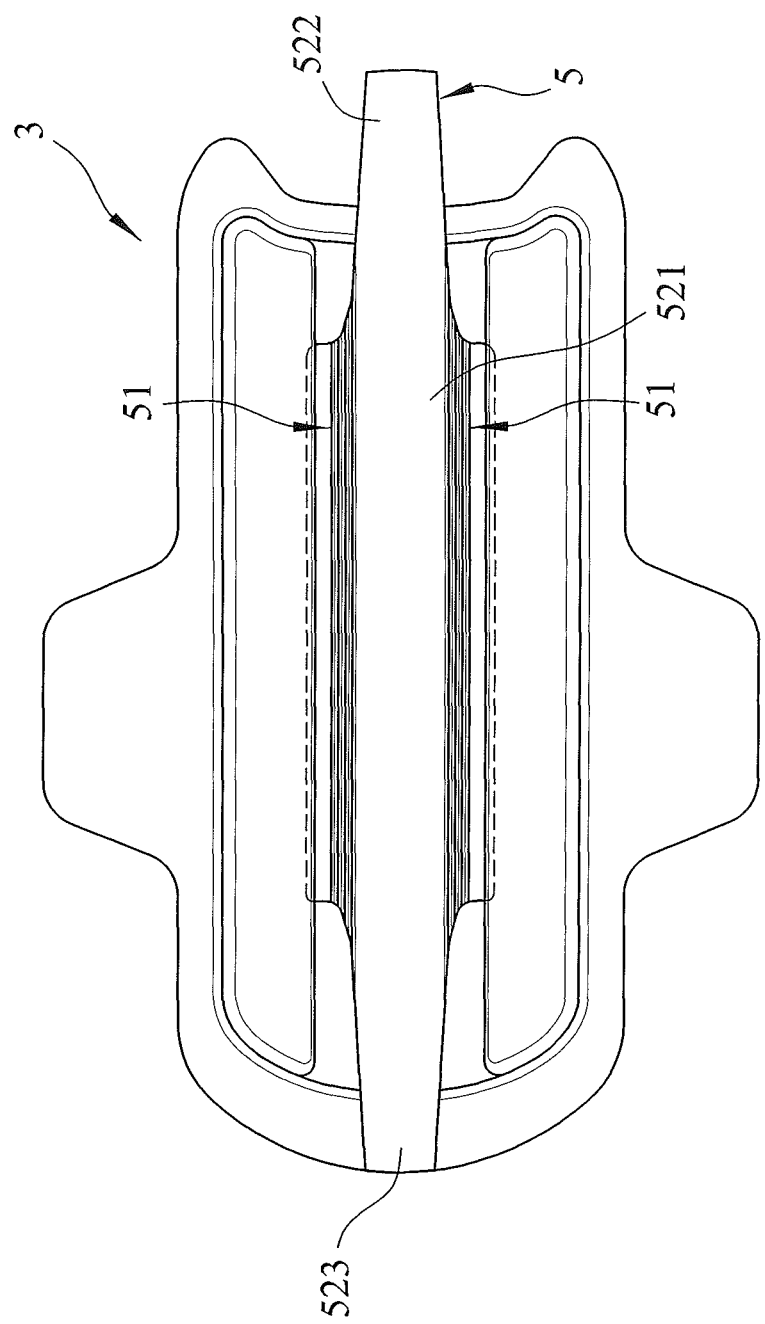
FIG. 15 is a top view of the fourth embodiment of the sanitary napkin of the present invention.
Figure 16:
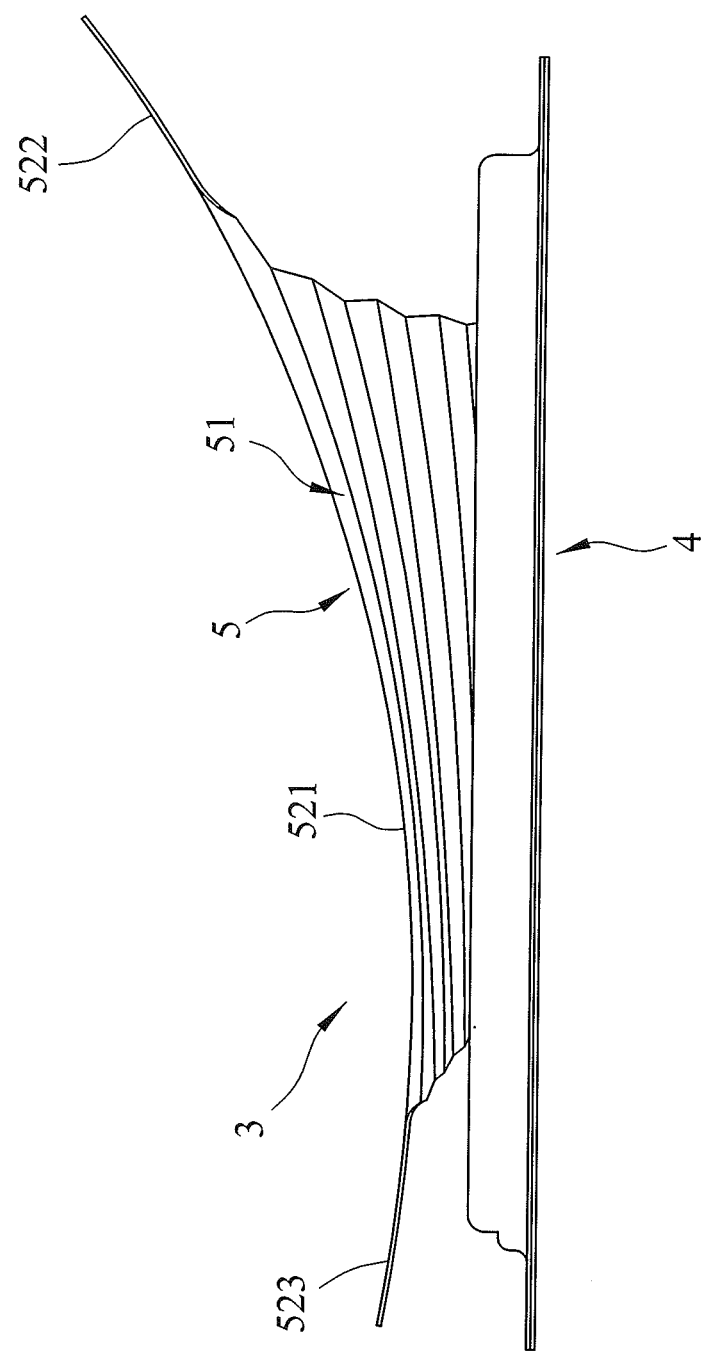
FIG. 16 is a view of the lateral aspect of the fourth embodiment.

Referring to FIGS. 15 and 16, the fourth embodiment of the sanitary napkin 3 of this invention is shown to be generally identical to the first embodiment, and the only difference between the two resides in that the pull piece 52 of the flow-guide unit 5 further includes a front extension portion 523 extending outwardly from a front end of the main body portion 521 opposite the rear extension portion 522. Through this, the user can pull either the front extension portion 523 or the rear extension portion 522. Hence, use of this embodiment is very convenient.

Figure 17:
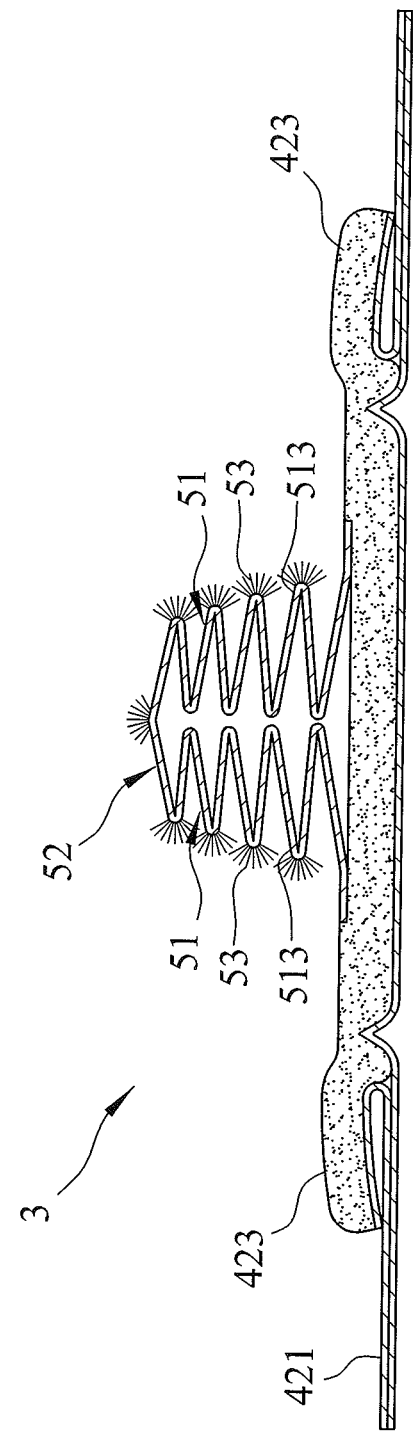
FIG. 17 is a sectional view of the fifth embodiment of the sanitary napkin of the present invention.

Referring to FIG. 17, the fifth embodiment of the sanitary napkin 3 of this invention is shown to be generally identical to the second embodiment. Particularly, the flow-guide unit 5 further includes a plurality of liquid-absorbent fluffs 53 provided on the outer junction sections 513 of the flow-guide members 51 and on an intermediate portion of the pull piece 52. The only difference between the fifth and second embodiments resides in that the pull piece 52 of the flow-guide unit 5 further includes a front extension portion 523 (see FIG. 15) as described in the fourth embodiment. The versatility of the sanitary napkin 3 can be enhanced using the fifth embodiment. It should be noted herein that, in this embodiment, the liquid-blocking portions 423 can also be turned inside out relative to the connecting portion 421. The advantages of the other embodiments can be achieved using the fifth embodiment.

Figure 18:
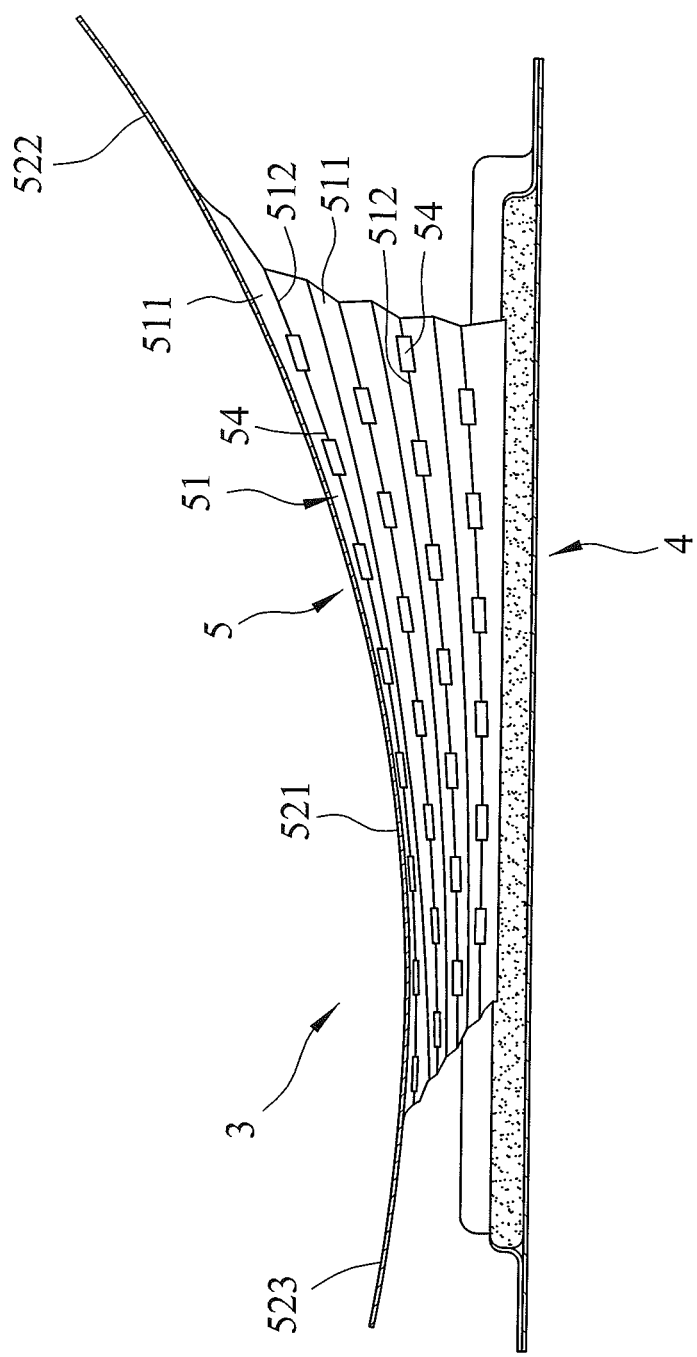
FIG. 18 is a sectional view of the sixth embodiment of the sanitary napkin of the present invention.

Referring to FIG. 18, the sixth embodiment of the sanitary napkin 3 of this invention is shown to be generally identical to the third embodiment. Particularly, each flow-guide member 51 of the flow-guide unit 5 further includes a plurality of vent holes 54 formed in the inner junction sections 512. The only difference between the sixth and third embodiments resides in that the pull piece 52 of the flow-guide unit 5 further includes a front extension portion 523 as described in the fourth embodiment. The versatility of the sanitary napkin 3 can be enhanced using the sixth embodiment.

In sum, the pull piece 52 can be pulled by the user to pull upward the flow-guide members 51 and move the same into the intergluteal cleft 61 of the user to achieve a good contact effect, thereby preventing blood leakage during sleep. Furthermore, through the presence of the flow-guide members 51, a space is maintained between the user's buttocks 62 and the main pad body 4 of the sanitary napkin 3 to resolve the problem of ventilation. Moreover, since the flow-guide members 51 are directly connected to the absorbent body 43, the liquid absorbing ability of the invention is rapid so that the user can be kept dry. In addition, the pull piece 52 can be fixed, so that the flow-guide members 51 will not easily be displaced when the user is walking. Therefore, the objective of this invention can be realized.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the invention. It should be further appreciated that in the description, various features are sometimes grouped together in a single embodiment, figure, or description thereof for the purpose of streamlining the disclosure and aiding in the understanding of various inventive aspects.

While the present invention has been described in connection with what are considered the most practical embodiments, it is understood that this invention is not limited to the disclosed embodiments but is intended to cover various arrangements included within the spirit and scope of the broadest interpretation to encompass all such modifications and equivalent arrangements.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A sanitary napkin comprising:
    a main pad body including a lower pad layer, an absorbent body disposed on said lower pad layer, and an upper pad layer cooperating with said lower pad layer to confine therebetween said absorbent body; and
    a flow-guide unit disposed on said main pad body and including two flow-guide members and a pull piece, with each of said two flow-guide members having a top end and a bottom end, with said bottom ends of said two flow-guide members connected to a top surface of said absorbent body and spaced apart from each other, with each of said two flow-guide members including a plurality of flow-guide sections, with the flow-guide sections stacked in a top-bottom direction and foldably connected to each other, a plurality of inner junction sections each formed between inner ends of two adjacent ones of the plurality of flow-guide sections, and a plurality of outer junction sections each formed between outer ends of two adjacent ones of the plurality of flow-guide sections, with said pull piece connected to said top ends of said two flow-guide members, and configured to be pulled to move said two flow-guide sections relative to said absorbent body from a folded position, in which said flow-guide sections of each of said two flow-guide members are stacked one upon the other, to an extended position, in which said outer junction sections of each of said two flow-guide members are spaced apart from each other, wherein widths of said flow-guide sections of each of said two flow-guide members gradually decrease from bottom to top when said flow-guide sections are in the folded position.

2. The sanitary napkin as claimed in claim 1, wherein each plurality of inner junction sections of said two flow-guide members is proximate to the other when said two flow-guide members are in the folded position.

3. The sanitary napkin as claimed in claim 1, wherein said upper pad layer has a connecting portion connected to said lower pad layer, and wherein the sanitary napkin further comprises two liquid-blocking portions extending inwardly from an inner periphery of said connecting portion, disposed on said top surface of the absorbent body, and spaced apart from each other in a left-right direction, with said connecting portion surrounding said liquid-blocking portions, and with said two liquid-blocking portions respectively proximate said bottom ends of said two flow-guide members.

4. The sanitary napkin as claimed in claim 3, wherein said two liquid-blocking portions are turnable inside out relative to said connecting portion to expose said top surface of said absorbent body.

5. The sanitary napkin as claimed in claim 4, wherein each of said two liquid-blocking portions has an inner side made of a liquid-absorbing material and an outer side made of a liquid impermeable material.

6. The sanitary napkin as claimed in claim 1, wherein said pull piece of said flow-guide unit has a main body portion connected to said top ends of said two flow-guide members, and at least one extension portion extending outwardly from said main body portion.

7. The sanitary napkin as claimed in claim 1, wherein said flow-guide unit further includes a plurality of liquid-absorbent fluffs provided on each plurality of outer junction sections of said two flow-guide members.

8. The sanitary napkin as claimed in claim 7, wherein each of said two flow-guide members further includes a plurality of vent holes formed in its plurality of inner junction sections.

9. The sanitary napkin as claimed in claim 8, wherein said vent holes formed in each of said plurality of inner junction sections are spaced apart from each other in a front-rear direction, and wherein vent holes in two adjacent ones of said inner junction sections are staggered with respect to each other.

10. The sanitary napkin as claimed in claim 7, wherein said pull piece of said flow-guide unit has a main body portion connected to said top ends of said two flow-guide members, with two extension portions extending outwardly and respectively from front and rear ends of said main body portion.

11. The sanitary napkin as claimed in claim 1, wherein each of said two flow-guide members further includes a plurality of vent holes formed in its plurality of inner junction sections.

12. The sanitary napkin as claimed in claim 11, wherein said vent holes formed in each of said plurality of inner junction sections are spaced apart from each other in a front-rear direction, and wherein vent holes in two adjacent ones of said inner junction sections are staggered with respect to each other.

13. The sanitary napkin as claimed in claim 1, wherein said pull piece of said flow-guide unit has a main body portion connected to said top ends of said two flow-guide members, with two extension portions extending outwardly and respectively from front and rear ends of said main body portion.

* * * * *